United States Patent [19]
Hagen et al.

[11] Patent Number: 4,873,973
[45] Date of Patent: Oct. 17, 1989

[54] MULTI-PART NEUTRAL ELECTRODE FOR AN HF SURGICAL INSTRUMENT

[75] Inventors: Uwe Hagen, Forchheim; Udo Redler, Effeltrich, both of Fed. Rep. of Germany

[73] Assignee: Siemens Aktiengesellschaft, Berlin and Munich, both of Fed. Rep. of Germany

[21] Appl. No.: 184,460

[22] Filed: Apr. 21, 1988

[30] Foreign Application Priority Data

Jul. 13, 1987 [DE] Fed. Rep. of Germany ....... 3723128
Sep. 3, 1987 [DE] Fed. Rep. of Germany ....... 3729516

[51] Int. Cl.4 .............................................. A61B 17/39
[52] U.S. Cl. ................................. 128/303.13; 128/798; 439/822; 439/833; 439/861; 439/909
[58] Field of Search ........... 128/303.13, 908, 639–641, 128/644, 798, 802; 439/59, 67, 77, 790, 792, 822, 829, 838, 861, 909

[56] References Cited

U.S. PATENT DOCUMENTS

| | | | |
|---|---|---|---|
| 3,642,008 | 2/1972 | Bolduc | 128/798 |
| 3,683,923 | 8/1972 | Anderson | 128/303.14 |
| 3,817,253 | 6/1974 | Gonser | 128/798 |
| 4,116,517 | 9/1978 | Selvin et al. | 439/67 |
| 4,353,372 | 10/1982 | Ayer | 128/640 |
| 4,384,582 | 5/1983 | Watt | 128/798 X |
| 4,538,865 | 9/1985 | Wakabayashi | 439/67 |
| 4,634,195 | 1/1987 | Shoemaker | 439/67 |

FOREIGN PATENT DOCUMENTS

8205363 8/1985 Fed. Rep. of Germany .
3544443 6/1987 Fed. Rep. of Germany .
3544483 6/1987 Fed. Rep. of Germany .

*Primary Examiner*—Lee S. Cohen
*Attorney, Agent, or Firm*—Lawrence C. Edelman

[57] ABSTRACT

A neutral electrode comprising several partial electrodes having respective electrical connections disposed on a carrier having a link to which the electrical connections lead. In the link, and specifically asymmetrically to the connections, a first and a second opening are provided. When a connecting clamp is connected to the electrode, these openings are engaged by projections which are arranged on the inside surfaces of two clamping elements of the connecting clamp.

20 Claims, 2 Drawing Sheets

MULTI-PART NEUTRAL ELECTRODE FOR AN HF SURGICAL INSTRUMENT

BACKGROUND OF THE INVENTION

1. Field of the Invention

The invention relates to a multi-part neutral electrode for a High-Frequency (HF) surgical instrument in which the partial electrodes are arranged on a common carrier and which has a connecting clamp with two elements held together by spring force between which the neutral electrode can be clamped.

2. Background of the Invention

A neutral electrode, which operates with two planar partial electrodes is known, for example, from German utility model patent No. 82 05 363.

It is known that a multi-part design of a neutral electrode is desirable if it is intended to indicate during surgical treatment whether or not the neutral electrode is in contact with the patient over a large area rather than a small area, using a monitor circuit. Such a monitor circuit is described in German Pat. No. 35 44 443 (corresponding to U.S. Ser. No. 929,561 filed Nov. 10, 1986). A monitor circuit is also described in U.S. Pat. No. 3,683,923.

A terminal clamp for a neutral electrode used in HF surgery is described in German Pat. No. 35 44 483 (corresponding to U.S. Ser. No. 929,570 filed Nov. 10, 1986), in particular in connection with FIGS. 3 to 5.

In a multi-part neutral electrode of the above-mentioned kind, which, in particular, can be designed as a disposable unit, ensurance should be given in a simple manner that holding means for a connecting clamp are available and that the certainty of contact with the connecting clamp is ensured when establishing connection.

Accordingly, it is an object of the invention to develop an electrode of the above-mentioned kind in such a way that a positive mechanical connection between the electrode and the connection cable connectable with a connecting clamp to the electrode, is ensured. Moreover, ensurance is to be provided that when connecting the connecting clamp, the electrical connections are not mistaken. Lastly, a connecting clamp is to be provided with which the electrode is connectable.

SUMMARY OF THE INVENTION

In accordance with the principles of the invention, these objects are solved by providing a multi-part neutral electrode for an HF surgical instrument in which the partial electrodes are arranged on a common carrier and wherein a connecting clamp having two clamp elements held together by spring force are used to clamp to the electrode. The carrier is provided on an edge with a link into which parallel electrical connections of the partial electrodes lead. An opening is provided in the link and arranged next to the parallel connections and outside the center of the link. One of the two clamp elements of the connecting clamp is provided on its inner surface with a projection.

The connection link of the electrode, preferentially built as disposable item, receives during its production preferentially on one margin side of the connection site, i.e., asymmetrically, an opening or a hole. The mechanical projection engages this opening when the cable connecting clamp is properly connected.

The projection (latching pin) is asymmetrically arranged in the one element and a retaining opening in the opposing element of the connection clamp, as well as the asymmetrically arranged opening (hole) in the link of the multi-part electrode, could lead when used inappropriately to so-called "tilting". By tilting is meant a rotation of the planar electrode around the axis of the projection (latching pin), and specifically in the manner that the electrical connections of the electrode are not precisely gripped by the contacts. If the electrical connections and the contacts are built longitudinally extended, which is frequently the case, the contacts can, under certain circumstances, grasp several connections simultaneously, which, of course, leads to inoperability. In order to preclude tilting when the electrode is held by the connecting clamp, according to an improved embodiment of the invention, it is suggested that a further opening be provided in the link which preferentially is also asymmetrically arranged with respect to the electrical connection. It is further suggested, that one of the two elements is provided on its inner surface with a further projection, which is also preferentially arranged asymmetrically with respect to the electrical contacts for the electrical connection of the electrode. The further opening and the further projection can be arranged on the same side as the previously-mentioned opening and the previously-mentioned projection.

Other features and advantages of the invention will be apparent from the description of the preferred embodiments, and from the claims.

For a fuller understanding of the present invention, reference should now be made to the following detailed description of the preferred embodiments of the invention and to the accompanying drawings.

DETAILED DESCRIPTION OF THE PREFERRED EMBODIMENT

Figure 1:
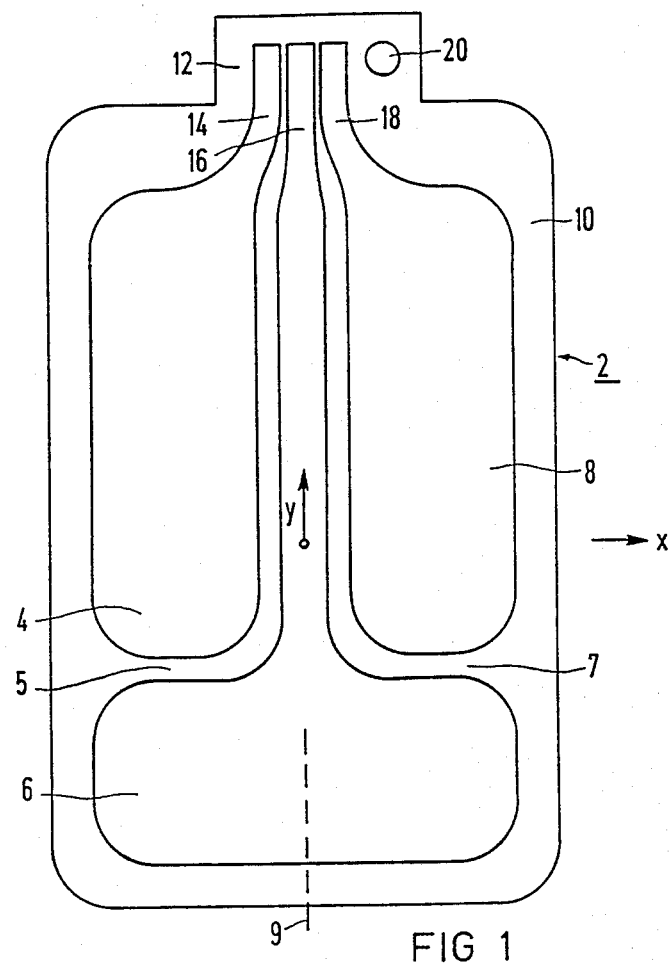
FIG. 1 illustrates a plan view of a three-part neutral electrode for an HF surgical instrument constructed in accordance with the principles of the invention.

As shown in FIG. 1, a neutral electrode 2 for an HF surgical instrument comprises three planar partial elecrodes 4, 6 and 8, separated from each other by insulating strips 5 and 7 having poor electrical conductivity. Partial electrodes 4, 6 and 8 are essentially rectangular but with rounded-off corners. With a multi-part neutral electrode 2 of this nature it can be determined, using a monitor circuit, whether it is in secure contact with a patient or has completely or partially fallen off. A suitable monitor circuit is described, for example, in the forenoted DE-OS No. 35 44 443. Partial electrodes 4 and 8 are arranged next to each other in the x direction. Partial electrode 6 is T-shaped, with the thin foot of the T lying between partial electrodes 4 and 8, thereby forming insulating strips 5 and 7. Outer partial elecrodes 4 and 8 are illustrated as being of equal size and positioned longitudinally, so that the main longitudinal axis 9 of the electrode coincides with the y direction. Partial electrodes 4, 6 and 8 consist in each instance of a metal foil or of a metal mesh and are fastened next to each other on one side of a flexible flat carrier 10. Carrier 10, which can preferentially be self-adhesive and consist of a substantially electrical insulative material such as rubber, is essentially rectangular. In the present embodiment carrier 10 is longer in the y direction than in the perpendicular x direction and projects at its edges somewhat beyond partial electrodes 4, 6, and 8.

Deviating from the representation in FIG. 1, frequently and preferentially the approach will be to select the surface area of all three partial electrodes 4, 6 and 8 to be identical.

At the upper edge of rectangular carrier 10, against which the base of the T-shaped partial electrode 6 lies, an extension, support or link 12 for an electrical line connection is provided. Link 12 receives electrical connections 14, 16 and 18 of partial electrodes 4, 6 and 8, i.e., electrical connections 14, 16 and 18 turn into the region of link 12 and end shortly before its outer edge. On link 12 connections 14, 16 and 18 extend parallel to each other and are closely adjacent. As can be seen, their three electrical terminal points are arranged close to each other on the partial electrodes 4, 6 and 8. This allows keeping the impedance difference low, i.e., to establish symmetrical electrical conditions.

A first opening 20 is provided in link 12. This is a round hole, the material of which can be reinforced around the margin. Opening 20 is arranged next to parallel connections 14, 16 and 18 outside of the center of link 12, i.e., asymmetrically. Its function is, as will become clear, to both mechanically secure a cable connecting clamp and for ensuring the certainty of the connections when the connection clamp is connected. Opening 20 is engaged by a projection of the connection clamp when the connection is established.

Figure 2:
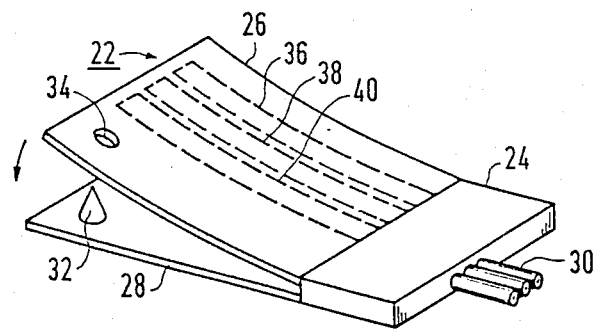
FIG. 2 illustrates a perspective view of a connecting clamp for connection to the electrode according to FIG. 1.

FIG. 2 shows schematically a connecting clamp 22, which consists of a basic body 24 and of two clamping elements 26 and 28 held together by spring force. A connecting cable consisting of three connecting lines is designated by reference numeral 30. The clamp according to FIGS. 3 to 5 of the forenoted DE-OS No. 35 44 483 is somewhat similar. However, as can be seen in FIG. 2 herein, the lower one of elements 26 and 28 is provided with a projection 32 projecting into the interspace. Projection 32 in the present embodiment is in the shape of a cone. In opposing upper element 26, in the corresponding site, a retaining opening 34 is located into which projection 32 fits in the closed position of connecting clamp 22. In a view from above, projection 32 is located next to contacts or connecting paths 36, 38 and 40 for the electrical connection of electrode 2. These connections or contacts 36, 38 and 40 can themselves be formed as elastic metal strips. Since they are on the inside of clamp 22, they are indicated by dashed lines.

During operation of electrode 2, projection 32 reaches through opening 20 into retaining opening 34. In this closed position, contacts 36, 38 and 40 are pressed under spring force against electrical connections 14, 16 and 18, respectively, of partial electrodes 4, 6 and 8, so that good electrical contact is established. Hence, it can be stated that due to opening 20 and projection 32, a certainty of mechanical securement between electrode 2 and connecting clamp 22 is ensured. In the operating room this is particularly advantageous, since, during a pull on cable 30, for example due to stumbling, it cannot readily be pulled from electrode 2. It should also be noted as advantageous that a certain electrical safety for measuring the HF partial current in partial electrodes 4, 6 and 8 results, since through the engagement of the eccentrically arranged opening 20 by projection 32, electrical connections 36, 38 and 40 cannot be mistaken. Lastly, it should be noted as advantageous the exclusion as a possible error source, that contacts 36, 38 and 40 of connecting clamp 22 make contact on the insulated backside of electrode 2.

Figure 3:
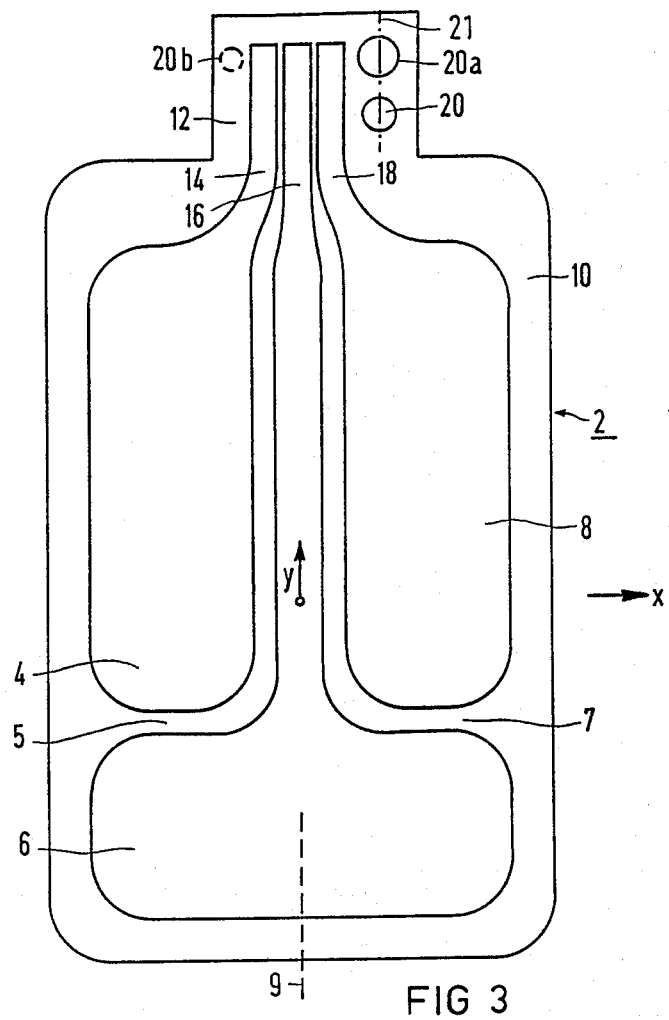
FIG. 3 illustrates a three-part neutral electrode for an HF surgical instrument with a further opening for assisting centering.
Figure 4:
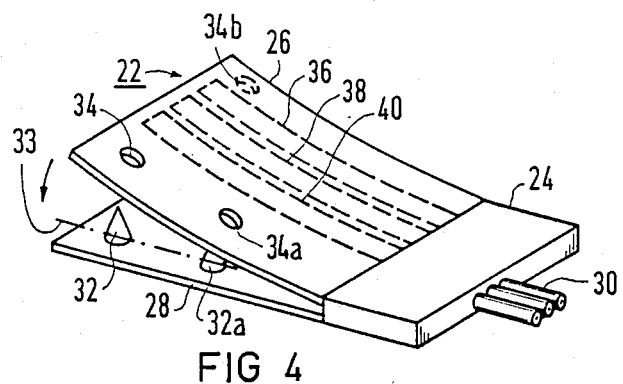
FIG. 4 illustrates a perspective view of a connecting clamp for connection to the electrode of FIG. 3.

In the embodiment according to FIGS. 3 and 4 a further or second opening 20a is provided in link 12. It is preferential to also arrange opening 20a asymmetrically with respect to the electrical connections. In the present case, openings 20 and 20a are arranged on a line 21, which is parallel to the main longitudinal axis 9. Alternatively, another asymmetrical position of second opening 20a could also be chosen. This is made clearer by a second opening 20b being illustrated in dashed lines which are on the other side of connections 14, 16 and 18 of link 12. The last mentioned opening 20b can also be present in addition to the first and second openings 20 and 20a. The two openings 20 and 20a or 20 and 20b are spaced at a given distance; therefore, if a pin or projection of the connecting clamp is lead through both openings 20 and 20a or 20 and 20b, potential tilting of connecting clamp 22 with respect to electrode 2 is precluded.

Compared to the embodiment according to FIGS. 1 and 2, according to FIG. 3 a longer side edge of connecting link 12 is available. This ensures better side guidance. Furthermore, due to the enlarged contact surface and second opening 20a or 20b, the form of closure between connecting clamp 22 (cable plug) and electrode 2 is improved. Thus, when connecting, the precision of alignment is increased and the contacts always take hold only of the assigned connections 14, 16 and 18 of electrode 2 for which they are intended.

It should also be pointed out that openings 20 and 20a or 20 and 20b can be unequal size. This facilitates taking hold of electrode 2 and increases the precision of alignment. In particular, second opening 20a or 20b should be larger than first opening 20 (as is shown in the case of opening 20a).

In FIG. 4 a connecting clamp 22 is schematically illustrated, which consists of a basic body 24 and two clamping elements 26 and 28 held together by spring force. The connecting cable 30 consists of three connecting lines.

As can be seen in FIG. 4, the lower of elements 26 and 28 is provided on one side with a projection 32 projecting into the interspace. Projection 32 has in the present embodiment the shape of a cone. In its place a pin of cylindrical shape could also be fastened on the clamping element 28. In an opposing upper element 26 at a corresponding site, a first retaining opening 34 is provided. Projection 32 engages it in the closed position of connecting clamp 22. Furthermore, lower clamping element 28 carries on its inside, and specifically near the basic body 24, an additional projection 32a. On a corresponding site of upper clamping element 26, a second retaining opening 34a is provided. When viewed from above, projections 32 and 32a are arranged next to the longitudinal contacts or connecting paths 36, 38 and 40 for the electrical connection of electrode 2. The latter are arranged parallel to each other. Projections 32 and 32a are arranged on a line 33, which, when connecting clamp 22 is closed, extends parallel to longitudinal electrical contacts 36, 38 and 40. These connections or contacts 36, 38 and 40 are fastened on the inner surface of upper clamping element 26, and therefore are shown in dashed lines. Connections or contacts 36, 38 and 40 can instead be themselves fashioned as elastic metal strips.

In the present embodiment projections 32 and 32a are arranged on the same clamping element 28. Instead, they can also be fastened, projecting into the interspace, on different clamping elements 26 and 28. Furthermore, another asymmetrical arrangement could be chosen, for example, such as was discussed in conjunction with additional opening 20b in FIG. 3. This is shown by opening 34b on the other side of contacts 36, 38 and 40, drawn in dashed lines.

During operation of electrode 2, connecting clamp 22 has one end connected to the HF surgical instrument and another end clamped to link 12. This allows projection 32 to engage the first retaining opening 34 through the first opening 20; and correspondingly allows the second projection 32a to engage the second retaining opening 34a through the second opening 20a. In this closing position, the longitudinal contacts 36, 38 and 40 are pressed by spring force against the correspondingly longitudinal connections 14, 16 and 18, respectively, of partial electrodes 4, 6 and 8, respectively, so that good electrical contact is established. Due to the fact that for locking in the closed position, two combinations of projection/opening/retaining opening 32/20/34, 32a/20a/34a or 32b (not shown)/20b/34b are used, potential tilting of connecting clamp 22 is excluded. In the closed position, due to the alignment of lines 21 and 33, the connections 14, 16 and 18 parallel to it coincide in the region of the link 12 with contacts 36, 38 and 40, respectively.

Thus, there has been shown and described novel apparatus for providing a multi-part neutral electrode and connecting clamp which fulfills all the objects and advantages sought therefor. Many changes, modifications, variations and other uses and applications of the subject invention will, however, become apparent to those skilled in the art after considering this specification and the accompanying drawings which disclose a preferred embodiment thereof. For example, the various alternative constructions already noted in the specification could be used. All such changes, modifications, variations and other uses and applications which do not depart from the spirit and scope of the invention are deemed to be covered by the invention which is limited only by the claims which follow.

What we claim is:

1. A multi-part neutral electrode for an HF surgical instrument having partial electrodes arranged on a common carrier, in combination with a connecting clamp including two facing elements having respective inner surfaces urged together by spring force, one of said elements including electrical contacts therein and said two elements releasably clamping said neutral electrode for making electrical connection thereto, wherein:
    an edge portion of said carrier is provided with an extension, said carrier extension having parallel electrical connections thereon leading from said partial electrodes;
    said carrier extension including first and second openings arranged asymmetrically with respect to said parallel electrical connections and offset from the center of said carrier extension; and
    one of the two facing elements of said connecting clamp is provided on its inner surface with first and second projections located for alignment with said first and second openings of said carrier extension.

2. An electrode combination according to claim 1, wherein:
    said openings are reinforced on their margins.

3. An electrode combination according to claim 1, wherein:
    said projections are arranged next to said electrical contacts of said connecting clamp for electrical connection of said electrode to said clamp.

4. An electrode combination according to claim 1, wherein:
    said projections are the shape of a cone and the other of said two clamping elements is provided with retaining openings for receiving the projections when said clamp is in a closed position.

5. An electrode combination according to claim 1, wherein:
    said two openings are arranged on a line which lies parallel to a main longitudinal direction of said carrier.

6. An electrode combination according to claim 5, wherein:

7. An electrode combination according to claim 1, wherein:
    said electrical connections of said carrier extension extend parallel to a line which lies parallel to a main longitudinal direction of said carrier.

8. An electrode combination according to claim 1, wherein:
    said two openings are of unequal size.

9. An electrode combination according to claim 1, wherein:
    said carrier extension includes a third opening therein; and
    said one of said two facing elements of said connecting clamp is provided on its inner surface with a further projection which is also arranged asymmetrically with respect to said parallel electrical connections and is aligned with said third opening of said carrier extension.

10. An electrode combination according to claim 1, wherein:
    the other of said two facing elements of said connecting clamp is provided with retaining openings which the first-mentioned projections project into when said clamp is in a closed position, and that for said further projection an additional retaining opening is provided.

11. An electrode combination according to claim 9, wherein:
    said two first mentioned projections are arranged on the same one of said two elements.

12. An electrode combination according to claim 9, wherein:
    said electrical contacts have a longitudinal shape and extend parallel to each other, and said two first mentioned projections are arranged on a line which in the closed position of said clamp extends parallel to said electrical contacts.

13. A multi-part neutral electrode for an HF surgical instrument having a plurality of partial electrodes arranged on a common carrier, wherein:
    an edge portion of said carrier is provided with an extension, said carrier extension having a corresponding plurality of parallel electrical connections thereon leading from respective ones of said plurality of partial electrodes; and said carrier extension includes first and second openings arranged asymmetrically with respect to said parallel electrical connections and offset from the center of said carrier extension.

14. An electrode according to claim 13, wherein:
said openings are reinforced on their margins.

15. An electrode according to claim 13, wherein:
said two openings are arranged on a line which lies parallel to a main longitudinal direction of said carrier.

16. An electrode according to claim 15, wherein:
said electrical connections of said carrier extension extend parallel to each other and parallel to said line.

17. An electrode according to claim 15, wherein:
said two openings are of unequal size.

18. A multi-part neutral electrode for an HF surgical instrument having a plurality of partial electrodes arranged on a common carrier, wherein:
an edge portion of said carrier is provided with an extension, said carrier extension having a corresponding plurality of parallel electrical connections thereon leading from respective ones of said plurality of partial electrodes; and
said carrier extension includes first and second openings arranged asymmetrically with respect to said parallel electrical connections and on a line which lies parallel to a main longitudinal direction of said carrier, said line being offset from the center of said carrier extension.

19. A multi-part neutral electrode for an HF surgical instrument having a plurality of partial electrodes arranged on a common carrier, in combination with a connecting clamp, wherein:
an edge portion of said carrier is provided with an extension, said carrier extension having a corresponding plurality of parallel electrical connections thereon leading from respective ones of said plurality of partial electrodes;
said carrier extension includes first and second openings arranged asymmetrically with respect to said parallel electrical connections and offset from the center of said carrier extension; and
said connecting clamp includes a pair of opposed clamping elements urged against one another by spring force, said clamping elements including a plurality of electrical contacts therein for providing electrical connection to said electrical connections of said neutral electrode when said carrier extension of said neutral electrode is positioned between said opposed clamping elements, one of said two clamping elements being provided, on its surface which opposes said other clamping element, with first and second projections which are located so as to be aligned with said first and second openings of said carrier extension when said carrier extension is positioned between said opposing clamping elements.

20. An electrode combination according to claim 19, wherein:
said projections are arranged next to said electrical contacts of said connecting clamp for electrical connection of said neutral electrode to said connecting clamp.

* * * * *